US00PP18668P2

(12) United States Plant Patent
Bradford

(10) Patent No.: US PP18,668 P2
(45) Date of Patent: Mar. 25, 2008

(54) INTERSPECIFIC TREE NAMED 'BLACKRED III'

(50) Latin Name: ***Prunus* sp.**
Varietal Denomination: BLACKRED III

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/634,856

(22) Filed: Dec. 7, 2006

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP14,196 P2 9/2003 Bradford
PP16,369 P2 3/2006 Bradford

*Primary Examiner*—Kent Bell
*Assistant Examiner*—S. B. McCormick-Ewoldt

(57) ABSTRACT

The present invention relates to an interspecific tree and more particularly to a new and distinct variety broadly characterized by a medium size, vigorous, hardy, and productive tree. Being self-unfruitful, the present variety requires cross pollination from an apricot, plum, or interspecific that blooms during the early to mid season. The fruit matures under the ecological conditions described during late July, with first picking on Jul. 29, 2006. The fruit is uniformly large in size, black in skin color, clingstone in type, somewhat cordate in shape, red in flesh color, very firm in texture, and outstanding in flavor.

1 Drawing Sheet

Botanical classification: *Prunus* sp.
Varietal denomination: 'BLACKRED III'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'BLACKRED III'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During the blooming season of 2001 one such house containing an unnamed red plum was crossed by me in this manner. To pollinate this red plum, I selected bouquets from several sources of apricot and interspecific plum-apricot hybrid trees without keeping specific written details. Upon reaching maturity, the fruit from this red plum tree was harvested and the seeds were removed, cracked, stratified and germinated as a group with the label "H8 42P". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'Plumsweettwo' (U.S. Plant Pat. No. 14,196) plum by being self-unfruitful and by producing fruit that ripens in late July, that is red in flesh color, and that is clingstone in type, but is distinguished therefrom by producing much more pollen, by being more productive, and by producing fruit that is black instead of purple in skin color, that is larger in size, that is somewhat cordate in shape, and that has less freckling on the skin.

SUMMARY OF VARIETY

The present interspecific variety is characterized by a medium size, vigorous, hardy, and productive tree. Being self-unfruitful, the pressed variety requires cross pollination from an apricot, plum, or interspecific that blooms during the early to mid season, such as 'Plumsweet V' (U.S. Plant Pat. No. 16,369) interspecific. The present variety's abundance of blossoms and pollen entices strong bee activity to facilitate pollination. The fruit matures under the ecological described during late July, with first picking on Jul. 29, 2006, and will hang on the tree for about twelve more days. The fruit is uniformly large in size, black in skin color, clingstone in type, somewhat cordate in shape, red in flesh color, very firm in texture, and outstanding in flavor.

DRAWING

The accompanying photograph consists of four whole fruits positioned to display the characteristics of the skin color and form, two halves of one fruit divided transversely to the suture plane to reveal the flesh and stone, typical leaves and insets depicting buds and blossoms as they appear on the tree.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Aug. 3, 2006, on the original tree during its fifth growing season. The flower and bud descriptions were developed during the previous blooming season. All major color code designations are by reference to the Inter-Society Color Council, National Bureau of Standards. Common color names are also used occasionally.

Parentage:
- *Seed parent.*—Unnamed red plum.
- *Pollen parent.*—Unknown.

Tree

Size: Medium reaching and maintaining a height of 10' [3.05 m.] and a spread of 7' [2.13 m.] after five growing seasons utilizing typical dormant pruning.

Vigor: Medium, responding typically to irrigation and fertilization. The variety grows about 4' [1.22 m.] of surplus top-growth during the spring and summer. The plant should be grown on a standard commercial rootstock for production purposes.

Growth: Spreading and open.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually required.

Fertility: Self-unfruitful, requiring cross pollination by a suitable early to mid seasonal blooming apricot, plum, or interspecific, such as 'Plumsweet V' (U.S. Plant Pat. No. 16,369).

Bearing: Reliable bearer, but dependent upon favorable weather during the blooming period.

Trunk:
- *Size.*—Medium, reaching a maximum diameter of 4½" [114 mm.] after the fifth growing season.
- *Texture.*—Shaggy.
- *Bark color.*—A Dark grayish reddish brown [47. d.gy.rBr] and Dark olive brown [96. d.OlBr] variegation with Moderate yellowish brown [77. m.yBr] cervices present.
- *Lenticels.*—Approximate Number Per Square Inch: 8. Color: Deep orange yellow [69. deep OY]. Typical Size: ⅛" [3.2 mm.] to 7/16" [11.1 mm.]. Shape: Eye-shaped to elongated.

Branches:
- *Size.*—Diameter of limb is 2¼" [57 mm.] measured 12" above the crotch, 1¼" [32 mm.] measured 12" above the first fork.
- *Texture.*—Smooth on first and second year wood, increasing roughness with age.
- *Color.*—1st Year Wood Topside: Light brown [57. l.Br]. 1st Year Wood Underside: Brilliant yellow green [116. brill.YG]. Older Wood: Deep yellowish brown [75. deep yBr].
- *Lenticels.*—Number Per Square Inch: More than 50 on second year wood. Color: Dark orange yellow [72. d.OY]. typical size: 1/32" [0.8 mm.] to 3/32" [2.4 mm.]. Shape: Elongated.

Leaves:
- *Size.*—Medium. Average Length: 3½" [89 mm.]. Average width: 1⅞" [48 mm.].
- *Arrangement.*—Alternate.
- *Thickness.*—Medium.
- *Form.*—Elliptical.
- *Apex.*—Acuminate.
- *Base.*—Acute with an average angle base angle of 75 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: 7/16" [11.1 mm.]. Average Thickness: 1/16" [1.6 mm.]. Color: Light yellow green [119. l.YG].
- *Stipules.*—Number: 2 per leaf, up to 6 per growing tip. Average Length: ¼" [6.4 mm.]. Color: Very yellow green [115. v.YG] becoming Moderate reddish brown [43. m.rBr] with age.
- *Glands.*—Number: Usually 2 per leaf. Position: Slightly alternate, positioned on base of blade. Size: Small. Form: Globose. Color: Brilliant yellow green [116. brill.YG] becoming Moderate yellowish brown [77. m.yBr] in the center with age.
- *Leaf buds.*—Pointed, medium.

Flower buds:
- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Color.*—White [263. White] with Strong pink [2. s.Pk] tips occasionally.

Flowers: Perfect, complete, perigynous, usually a single pistil, typically twenty-four or more stamens, five sepals and petal locations alternately positioned.
- *Average flower diameter.*—15/16" [23.8 mm.].
- *Number of petals.*—Five, no double blossoms observed.
- *Petal shape.*—Circular to oval.
- *Petal margin.*—Smooth to slightly wavy.
- *Average petal diameter.*—7/16" [11.1 mm.].
- *Average petal length.*—½" [12.7 mm.].
- *Petal apex.*—Rounded.
- *Petal base.*—Rounded to somewhat obtuse.
- *Petal color.*—White [263. White].
- *Anther color.*—Dark reddish orange [38. d.rO] over a Light yellow [86. l.Y] center.
- *Stigma color.*—Pale greenish yellow [104. p.gY].
- *Sepal color.*—Light yellow green [119. l.YG] with Grayish pink [8. gy.Pk] toward the margins and the base.
- *Sepal length.*—5/32" [4.0 mm.].
- *Sepal width.*—⅛" [3.2 mm.].
- *Average pistil length.*—9/16" [14.3 mm.].
- *Average stamen length.*—½" [12.7 mm.].
- *Fragrance.*—Moderate.
- *Pollen production.*—Abundant.

*Blooming period.*—Somewhat early, with 'Ambra' (unpatented).
*Onset of bloom.*—One percent on Feb. 7, 2006.
*Duration of bloom.*—One to two weeks, dependent on ambient temperature.
*Bloom density.*—Extremely heavy.
*Number per cluster.*—2 to 10, average 7.

FRUIT

Maturity when described: Firm ripe, Aug. 3, 2006.
Date of first picking: Jul. 29, 2006.
Date of last picking: Aug. 10, 2006.
Size: Uniform, large.
*Average diameter axially.*—2 7/16" [62 mm.].
*Average diameter across cheek plane.*—2 13/16" [71 mm.].
*Average diameter across suture plane.*—2 7/8" [73 mm.].
*Typical weight.*—6.9 ounces [196 grams].
Form: Uniform, symmetrical, somewhat cordate to globose.
*Longitudinal section form.*—Elliptical, cordate if viewed parallel to the suture.
*Transverse section through diameter.*—Round.
Suture: A line within a shallow groove extending from the base to the apex.
Ventral surface: Rounded, slightly lipped toward the base on both sides.
Lips: Equal.
Cavity: Flaring, circular to slightly elongated in the suture plane, suture showing on one side, Dark reddish orange [38. d.rO] stem markings typical.
*Depth.*—7/16" [11.1 mm.].
*Breadth.*—1 1/8" [28.6 mm.].
Base: Truncate, somewhat cordate if viewed parallel to suture.
Apex: Rounded to truncate.
Pistil point: An inconspicuous dot.
Stem: Medium.
*Average length.*—3/8" [9.5 mm.].
*Average width.*—1/8" [3.2 mm.].
Skin:
*Thickness.*—Medium.
*Surface.*—Smooth.
*Tenacity.*—Tenacious to flesh.
*Astringency.*—Moderate.
*Tendency to crack.*—Slight.
*Color.*—Black [267. Black] over a Very dark purplish red [260. v.d.pR] background with very small Light yellowish pink [28. l.yPk] freckling.
*Bloom.*—Abundant.
Flesh:
*Color.*—Light yellowish pink [28. l.yPk] with Moderate red [15. m.R] streaking stronger toward the skin.
*Surface of pit cavity.*—Moderate red [15. m.R] broken fibers when twisted from the stone.
*Amygdalin.*—Moderate.
*Juice.*—Moderate, rich.
*Texture.*—Firm, tough.
*Fibers.*—Abundant, fine.
*Ripens.*—Somewhat earlier toward the apex.
*Flavor.*—A tasty blend of acid and sugar, typically 18–20 brix.
*Aroma.*—Slight.
*Eating quality.*—Excellent.

STONE

Type: Clingstone.
Form: Oval.
Hilum: Narrow.
Base: Straight.
Apex: Obtuse with an average angle of 105 degrees.
Sides: Equal.
Surface: Rough throughout, one slight groove from base to apex on each side of dorsal fin.
External color of stone: Light yellowish brown [76. l.yBr].
Pit wall color when cracked: Strong brown [55. s.Br].
Cavity surface color: Light brown [57. 1.Br].
Average pit wall thickness: 1/16" [1.6 mm.].
Average width: 5/8" [15.9 mm.].
Average length: 3/4" [19.1 mm.].
Average breadth: 3/8" [9.5 mm.].
Tendency to split: Slight in wet season.
Kernel:
*Form.*—Oval.
*Skin color.*—Strong brown [55. s.Br].
*Pellicle color.*—Grayish brown [61. gy.Br].
*Vein color.*—Grayish brown [61. gy.Br].
*Taste.*—Slightly bitter.
*Viable.*—Yes.
*Average width.*—7/16" [11.1 mm.].
*Average length.*—1/2" [12.7 mm.].
*Amygdalin.*—Slight.

USE

Market: Fresh market and long distance shipping.
Keeping quality: Excellent. Fruit quality observed to remain in good condition in after 30 days in standard cold room at 36° Fahrenheit [2° Celsius].
Shipping quality: Excellent.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif. in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'Plumsweettwo' (U.S. Plant Pat. No. 14,196) plum by being self-unfruitful and by producing fruit that ripens in late July, that is red in flesh color, and that is clingstone in type, but is distinguished therefrom by producing much more pollen, by being more productive, and by producing fruit that is black instead of purple in skin color, that is larger in size, that is somewhat cordate instead of oblate in shape, and that has less freckling on the skin.

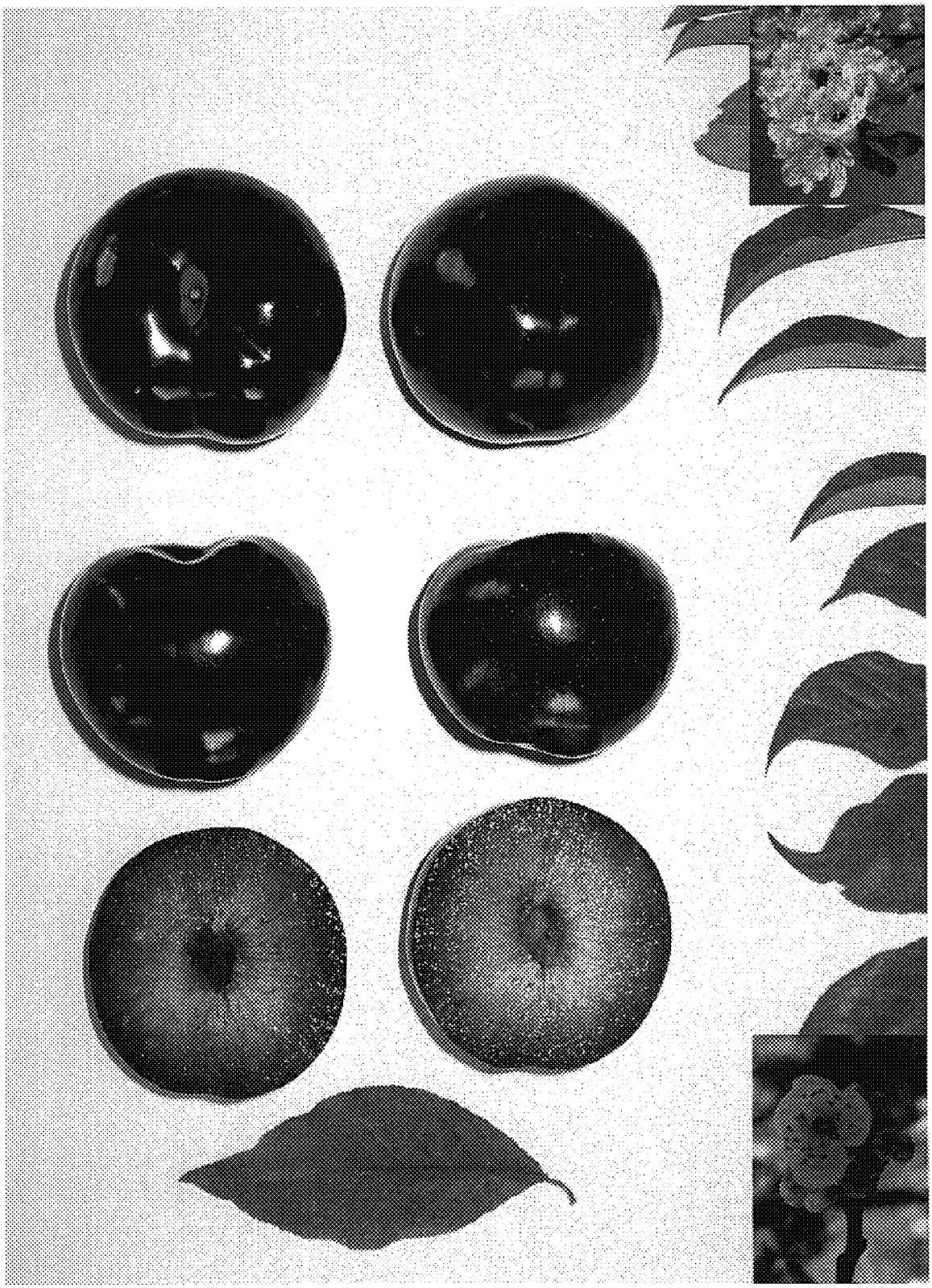

* * * * *